United States Patent [19]

Neier et al.

[11] 4,456,776

[45] Jun. 26, 1984

[54] PROCESS FOR THE PRODUCTION OF A LOWER ALIPHATIC ALCOHOL

[75] Inventors: Wilhelm Neier; Werner Webers; Wolf Ostwald, all of Rheinberg, Fed. Rep. of Germany

[73] Assignee: Deutsche Texaco Aktiengesellschaft, Hamburg, Fed. Rep. of Germany

[21] Appl. No.: 457,827

[22] Filed: Jan. 13, 1983

Related U.S. Application Data

[63] Continuation-in-part of Ser. No. 274,685, Jun. 17, 1981, abandoned.

[30] Foreign Application Priority Data

Jun. 27, 1980 [DE] Fed. Rep. of Germany ....... 3024146

[51] Int. Cl.$^3$ ............................................. C07C 29/04
[52] U.S. Cl. .................................................... 568/899
[58] Field of Search ........................................ 568/899

[56] References Cited

U.S. PATENT DOCUMENTS 3,994,983 11/1976 Webers ............................... 568/899

FOREIGN PATENT DOCUMENTS 809318 2/1959 United Kingdom .

OTHER PUBLICATIONS

Mace et al., "Chemical Engineering Progress", vol. 50, No. 8, Aug. 1954, pp. 385–395.

*Primary Examiner*—J. E. Evans
*Attorney, Agent, or Firm*—Robert A. Kulason; James J. O'Loughlin

[57] ABSTRACT

A process for continuously producing a lower aliphatic alcohol by the direct hydration of a lower aliphatic olefin having from 3 to 5 carbon atoms in the presence of a strongly acidic cation exchange resin catalyst the improvement which comprises presaturating the olefin feed with from about 0.3 to 1.8 weight percent of water prior to introducing the olefin feed into the reactor.

7 Claims, No Drawings

PROCESS FOR THE PRODUCTION OF A LOWER ALIPHATIC ALCOHOL

This is a continuation-in-part of U.S. patent application Ser. No. 274,685, filed June 17, 1981 and now abandoned.

BACKGROUND OF THE INVENTION

The instant invention relates to a process for the continuous production of a lower aliphatic alcohol, such as isopropanol and sec. butyl alcohol, by the direct hydration of the corresponding olefins, namely propene and n-butene, in the presence of a strongly acidic cation exchange resin catalyst in a single-tube reactor with discretionary diameter as fixed bed sump reactor.

In DE-AS No. 24 29 770 (second publication) a process for the continuous production of lower alcohols in the presence of strongly acidic cation exchange resins was disclosed. The alcohol obtained was removed overhead as vapor together with excess reaction gas. After separating the gas, 80% alcohol was obtained. However, in this process, the reaction water and reaction gas were separately preheated and evaporated. Since the reactor bed cools noticeably as the reaction proceeds and this after a traverse of only 0.8 to 1.2 meters in the reaction tube, the maximum practical tube diameter for this process is only about 100 mm. Therefore, the commercial reactors used for this process have been multi-tube reactors. When a sump operation is employed in these reactors, the uniform distribution of the gaseous and liquid phases presents difficulties.

The cooling effect observed during the course of the reaction was not understood. It is known from DA-AS No. 14 93 190 that gases under supercritical conditions absorb alcohols which can be recovered by pressure release or by heating at a constant pressure. On page 9, lines 10 through 23 and 53 through 67 of the last mentioned patent application, it is stated that the absorption and recovery of such alcohols or other materials does not cause noticeable cooling or heating effects in the system.

It has now been found that under supercritical conditions the propene/propane and n-butene/n-butane reaction gas mixtures, particularly under reaction conditions of 135° C. to 145° C. and min. 60 bar, and 155° to 165° C. and min. 40 bar, respectively, absorb 1.4 % wt. and 1.8 % wt. water, respectively, irrespective of the loading of gases with alcohol. Owing to the absorption of these amounts of water and also of the alcohol in the catalyst bed, the temperature in reactors having a large diameter, e.g. a diameter greater than 150 mm drops substantially after a short distance or passage of the reactants in the reactor even when the tube is externally heated. This occurs despite the heat of formation produced in the reaction of 37.6 KJ/mole for SBA and 50.2 KJ/mole for IPA with the result that the reaction nearly causes.

A method has been found which prevents the harmful cooling of the reactor bed in the above-described process.

The object of the present invention is to provide an improved process for the production of a lower aliphatic alcohol by the direct hydration of the corresponding aliphatic olefin in a large diameter single-tube sump reactor which facilitates the maintenance of a constant temperature and pressure in the reactor.

SUMMARY OF THE INVENTION

The method of the invention which is effective for providing a highly efficient process for the manufacture of a lower aliphatic alcohol comprises forming a mixture of a lower aliphatic olefin and water and passing the mixture upwardly through a tubular fixed bed reactor containing a strongly acidic cation exchange resin catalyst wherein the improvement comprises presaturating the olefin reactant with a selected amount of water prior to charging it to the reactor.

SPECIFIC EMBODIMENTS OF THE INVENTION

According to the method of this invention, a lower aliphatic alcohol having from 3 to 5 carbon atoms is prepared by presaturating an aliphatic olefin having from 3 to 5 carbon atoms with water to a certain degree and reacting the thus saturated aliphatic olefin with excess water in the presence of a strongly acidic cation exchange resin catalyst at a temperature ranging from about 120° C. to 180° C. and under a pressure ranging from about 40 to 200 bar.

The olefins that can be reacted in accordance with this process are the lower aliphatic olefins having from 3 to 5 carbon atoms. Specific examples of suitable olefins include propylene, 1-butene, 2-butene, isobutylene, 1-pentene, and mixtures of same with minor amounts of inert aliphatic hydrocarbons generally of similar carbon chain length. Examples of the latter include a butene-butane mixture consisting of 85% n-butene and a propane-propene mixture consisting of about 92% propene. Such a mixture should contain at least about 70% of olefin.

This reaction is generally conducted in the presence of an excess of water. Broadly, the ratio of water to olefin can range from about 0.5 to 10 moles of water per mole of olefin with the particularly preferred mole ratio being from 1 to 3 moles of water per mole of the olefin.

This reaction is conducted in the presence of a synthetic cation exchange resin catalyst which is generally employed in a highly acidic form containing sulfonic acid groups. More specifically, the catalyst is a hydrocarbon skeleton consisting of a copolymer of styrene and divinyl benzene consisting of 80 to 95% styrene and from about 20 to 5% divinyl benzene. This hydrocarbon skeleton is treated with a sulfur-containing acid until it becomes highly acidic with sulfonic acid groups. In general, the catalyst will contain from about 0.2 to 1 sulfonic acid groups per aromatic ring in a cation exchange resin.

This reaction is conducted at an elevated temperature and pressure. Broadly, the reaction is conducted at a temperature ranging from about 120° C. to 180° C. and at a pressure ranging from about 40 bar to 200 bar or above. The preferred temperature and pressure employed in the reaction varies according to the particular olefin being fed to the reactor. Thus, when the olefin being reacted is propene, it is preferred to employ a reaction temperature ranging from about 135° to 145° C. and to employ a minimum pressure of 60 bar. When the olefin reactant is n-butene, it is preferred to employ a reaction temperature ranging from 155° to 165° C. with the minimum pressure being 40 bar.

A critical feature of this process is the preparation and use of a water saturated olefin feed prior to the introduction of the olefin feed with water to the reactor containing the ion exchange resin catalyst. As previously noted, it has been discovered that the olefins employed in this process will absorb water. Propene will absorb up to 1.4 weight percent water and n-butene will absorb up to 1.8 weight percent of water. In order to realize the improvements of this invention, it is vital that the olefin feed be presturated with water prior to charging it to the reactor. In general, the olefin feed is presaturated with from about 0.3 to 1.8 weight percent of water based on the weight of the olefine feed. It is preferred, however, to presaturate the $C_4$-olefin with from 1.0 to 1.8 weight percent of water. In the case of a $C_3$-olefin feed stream, namely a propene-propane feed, a presaturation range from about 0.3 to 1.4 weight percent of water is effective. With a $C_4$ olefin feed system, such as a n-butene-n-butene mixture, the most effective presaturation range is from 1.0 to 1.8 weight percent of water. Subsequent to the presaturation step, the presaturated olefin is evaporated in the presence of part of the reaction water and passed into the reactor containing the ion exchange resin catalyst.

Presaturation of the olefin reactant is effected in a gas evaporator. The water intended for joint evaporation with the olefin is preferably fed into the evaporator together with the olefin. For evaporation, a four-shell multitube heat exchanger with a compensator has proven very suitable. By rerouting the vapor stream several times in the exchanger, good contacting of water and olefin is ensured. There is no criticality in the type of heat exchanger employed so long as effective presaturation of the olefin feed stream is accomplished.

It was surprising to find that this process permits the maintenance of a relatively steady reaction temperature in the reactor and avoids the earlier noted problem of cooling of the catalyst bed below reaction temperatures as the reaction mixture passes through it. By carefully selecting the amount of water to be evaporated together with the olefin feed the process can be made to proceed exothermally or weakly endothermally.

In contrast to other hydration processes, this process avoids the problem of substantial heat losses and the formation of inefficient or inactive catalyst zones in the reactor. Rather, it permits the maintenance of a relatively constant effective reaction temperature in the catalyst bed.

The following examples illustrate the practice of this invention.

COMPARISON EXAMPLE 1

300.3 kgs/h of a butane/butene mixture (85% n-butene=4,534 moles) and 204.0 kgs/h of water (=11,333 moles) are transferred to a reactor (inside diameter 500 mm, length 10 meters) packed with 1900 liters of stainless steel material and 1,700 liters of strongly acidic ion exchange resin catalyst. The water is previously heated to 155°–160° C. The feedgas is previously mixed with recycle gas evaporated in an evaporator, and is heated to 160° C. The reaction pressure is maintained at 60 bar. The secondary butyl alcohol is removed overhead together with excess $C_4$-gas. After releasing the pressure the alcohol is separated from the n-butane/n-butene mixture and removed. Most of the excess n-butane/n-butene mixture is recycled to the reactor. Part of it is removed as residual gas.

In this experimental setup a reaction temperature of 155° to 158° C. was measured in the catalyst bed after a distance of 20 cm. Despite exothermic reaction (37.6 KJ per mole of SBA hydration heat) and 100-mm-thick insulation the reaction temperature dropped after a short distance in the reactor falling to 115° C. to 120° C. at the reactor head. Owing to the noticeable temperature drop in the reaction bed, the average catalyst efficiency was only 0.4 mole of SBA per liter of catalyst per hour.

The experiment described in above comparison example was repeated employing a 9-bar steam heated coil to heat the reactor. Although the exterior wall temperature was 160° C. to 165° C., the temperature profile was only slightly improved. The average catalyst efficiency was 0.45 mole of sec. butyl alcohol per liter of catalyst per hour.

EXAMPLE 2

The procedure described in comparison Example 1 was altered so that by use of an additional dosing pump 54 kgs of the process water (total amount 204 kgs) were charged to the n-butane/n-butene mixture (feedgas and recycle gas=3,000 kgs/h) and transferred to the evaporator. Employing the same conditions as in comparison Example 1 (155° C. to 160° C., 70 bar) a temperature of 155° C. to 162° C. could be maintained in the reactor without additional heating or cooling. In the sump of a column, average amounts of 201.3 kgs (2,720 moles) of sec. butyl alcohol and 2.1 kgs (16.2 moles) of di-sec. butyl ether were obtained per hour as an approx. 99% purity crude alcohol. 101.5 kgs of n-butene and 46.4 kgs of n-butane were obtained as an approx. 59% mixture.

1.6 moles of sec. butyl alcohol and 0.0095 mole of ether were formed per liter of catalyst per hour.

COMPARISON EXAMPLE 3

The apparatus described in comparison Example 1 was used for the production of isopropyl alcohol. After evaporation and heating to 135° C. in the evaporator 231.3 kgs of a propane/propene mixture (92% propene) and 2,000 kgs of recycle gas were charged per hour to the reactor sump. 200 kgs of reaction water were transferred, heated to 135° C. and charged to the reactor bottom. The reaction pressure was maintained at 100 bar. The vaporous isopropyl alcohol was removed overhead together with excess reaction gas. After lowering the pressure to 20 bar the alcohol was separated from recycle gas in a column. After a distance of 20 cm in the reactor, the temperature was between 134° C. to 135° C. After a distance of 1.2 meters in the reactor, the temperature dropped to approx. 114° C. despite a heat of formation of 50.2 KJ/mole of isopropyl alcohol. About 0.5 mole of isopropyl alcohol was formed per liter of catalyst per hour.

COMPARISON EXAMPLE 4

57.7 kgs/h of a propene-propane mixture (92% propene=962 moles) and 50.0 kgs/h of water (=2,777 moles) were transferred to a reactor (inside diameter 250 mm, length 10 m) packed with 490 liters of stainless steel material and with 420 liters of strongly acidic ion exchange resin catalyst. The water was previously heated to 135° C. The feedgas was previously mixed with 500 kgs/h of recycle gas, was evaporated in evaporator and was heated to 135° C. The reaction pressure was maintained at 100 bar. The produced isopropyl alcohol was removed overhead together with excess $C_3$-gas. After releasing the pressure the alcohol was separated from the propane-propene mixture and removed. Most of the excess propane-propene mixture was recycled to the reactor. Part of it was removed as residual gas.

In this experimental setup a reaction temperature of about 135° C. was measured in the catalyst bed after a distance of 20 cm. Despite exothermic reaction (50.2 KJ per mole IPA hydration heat) and 100 mm-thick insulation the reaction temperature dropped considerably after a short distance in the reactor and only was of from 115° C. to 188° C. at the head of the reactor. Owing to the noticeable temperature drop in the reaction bed the average catalyst efficiency was only 0.5 mole of IPA per liter of catalyst per hour.

The experiment described in above comparison example was repeated additionally employing a 9-bar steam heated coil to heat the reactor. Although the exterior wall temperature was 135° C. to 140° C. the temperature profile was only slightly improved. The average catalyst efficiency was 0.55 mole of isopropyl alcohol per liter of catalyst per hour.

COMPARISON EXAMPLE 5

The procedure described in comparison example 4 was altered so that by use of an additional dosing pump 7.8 kgs of the process water (total amount 50 kg) were charged to the propane-propene mixture (feedgas and recycle gas=557.7 kgs/h) and jointly transferred to the evaporator. Employing the otherwise same conditions as in comparison example 1 (about 135° C. to 140° C., 100 bar) the excess reaction heat had now to be removed by quenching with a total of about 30 kgs/h of water (of about 25° C.) at three positions of the reactor (after distances of 1.5 m, 4 m and 7 m of the catalyst bed). Thereby more process water (80 kgs/h instead of 50 kgs/h) had to be desalted and recycled.

With a gas conversion of 75% based on the added amount of feedgas (55.7 kgs/h 92% propene) an average catalyst efficiency of 2.0 mole isopropyl alcohol per liter of catalyst per hour could be obtained. The selectivity was 98%.

If, under the same conditions, the quenching was discontinued, after a short time the reaction temperature raised with continously increasing rate of reaction. At about 160° C. to 170° C. the formation of byproducts (diisopropyl ether plus polymers) already was above 10–12%. Besides the lower selectivity with this procedure the obtained alcohol could not be made up as IPA-cosmetic grade because of strong odors.

EXAMPLE 6

The procedure described in comparison example 5 was altered so that by controlled presaturation of the propane-propene feedgas stream (555.7 kgs/h,) with water it was taken care for a very little excess of energy in the reactor. Therefore, about 2.5 kgs/h of water were admixed to the feedgas stream and jointly transferred to the evaporator. The rest amount of water for saturation of the gaseous phase (1.4%) (about 5.3 kgs/h) was evaporated in the reactor for energy balance. Using the same conditions as in comparison example 5 a reaction temperature of 135° to 140° C. could be maintained overall the reactor. At a gas conversion of 75% based on the amount of feed gas (55.7 kgs of a 92% propene) 55.44 kgs of isopropyl alcohol (924 mole) and 0.92 kgs of diisopropyl ether (9 moles) as an approx. 99% aqueous crude alcohol could be removed per hour at the sump of the column. 2.2 mole of isopropyl alcohol per liter catalyst per hour were formed. The selectivity was nearly 99%.

The foregoing examples illustrate the improvement brought about in the process of the invention which incorporates the essential presaturation step. Thus, examples 2 and 6 illustrate the best mode of operation of this novel process which facilitates the maintenance of a constant temperature and pressure in the reactor.

We claim:

1. A process for the continuous production of a lower aliphatic alcohol having from 3 to 5 carbon atoms by the direct catalytic hydration of a lower aliphatic olefin having from 3 to 5 carbon atoms with water which comprises reacting a reactant stream of said olefin with water in the presence of a strongly acidic cation exchange resin catalyst in a tubular fixed bed reactor by passing said reactants through said catalyst bed in upstream flow at a temperature ranging from about 120° C. to 180° C., at a pressure from about 40 to 200 bar and the water/olefin mole ratio ranging from about 0.5 to 10 moles of water per mole of said olefin, said tubular fixed bed reactor being characterized by having a cross-sectional diameter greater than 150 mm and said process having the tendency of substantially lowering the reaction temperature in said catalyst bed and impairing the reaction efficiency as said reactants pass through said catalyst bed, the step which comprises intimately contacting said heated reactant stream comprising said olefin and said water until said olefin has been presaturated with from about 1 to 1.8 weight percent of water prior to introducing said reactant stream into said reactor in order to maintain a relatively steady reaction temperature and efficient conversion of said olefin to said alcohol in said reactor.

2. A process according to claim 1 in which the water/olefin mole ratio ranges from about 1 to 3 moles of water per mole of said olefin.

3. A process for the continuous production of secondary butyl alcohol by the direct catalytic hydration of n-butene with water which comprises reacting a reactant stream of said n-butene with water in the presence of a strongly acidic cation exchange resin catalyst in a tubular fixed bed reactor by passing said reactants through said catalyst bed in upstream flow at a temperature ranging from about 155° C. to 165° C., at a pressure from about 40 to 200 bar and the water/olefin mole ratio ranging from about 1 to 3 moles of water per mole of said n-butene, said tubular fixed bed reactor being characterized by having a cross-sectional diameter greater than 150 mm and said process having the tendency of substantially lowering the reaction temperature in said catalyst bed and impairing the reaction efficiency as said reactants pass through said catalyst bed, the step which comprises intimately contacting said heated reactant stream comprising n-butene and water until said n-butene has been saturated with about 1 to 1.8 weight percent of water prior to introducing said reactant stream into said reactor in order to maintain a relatively steady reaction temperature and efficient conversion of said n-butene to secondary butyl alcohol in said reactor.

4. A process according to claim 3 having the tendency of lowering the reaction temperature in said catalyst bed to approximately 115°–120° C. and in which said tendency is counteracted by saturating said n-butene with about 1.8 weight percent water prior to introducing said reactant stream into said reactor.

5. A process for the continuous production for a lower aliphatic alcohol having from 3 to 5 carbon atoms by the direct catalytic hydration of a lower aliphatic olefin having from 3 to 5 carbon atoms with water which comprises reacting a reactant stream of said olefin with water in the presence of a strongly acidic cation exchange resin catalyst in a tubular fixed bed reactor by passing said reactants through said catalyst bed in upstream flow at a temperature ranging from about 120° C. to 180° C., at a pressure from about 40 to 200 bar and the water/olefin mole ratio ranging from about 0.5 to 10 moles of water per mole of said olefin, said tubular fixed bed reactor being characterized by having a cross-sectional diameter greater than 150 mm and said process having the tendency of substantially lowering the reaction temperature in said catalyst bed and impairing the reaction efficiency as said reactants pass through said catalyst bed, the step which comprises intimately contacting said heated reactant stream comprising said olefin and said water until said olefin has been saturated with from about 0.3 to 1.8 weight percent of water prior to introducing said reactant stream into said reactor in order to maintain a relatively steady reaction temperature and efficient conversion of said olefin to said alcohol in said reactor.

6. A process according to claim 5 in which the water/olefin mole ratio ranges from about 1 to 3 moles of water per mole of said olefin.

7. A process for the continuous production of isopropyl alcohol by the direct catalytic hydration of propene with water which comprises reacting a reactant stream of said propene with water in the presence of a strongly acidic cation exchange resin catalyst in a tubular fixed bed reactor by passing said reactants through said catalyst bed in upstream flow at a temperature ranging from about 135° C. to 145° C., at a pressure from about 40 to 200 bar and the water/olefin mole ratio ranging from about 1 to 3 moles of water per mole of said propene, said tubular fixed bed reactor being characterized by having a cross-sectional diameter greater than 150 mm and said process having the tendency of substantially lowering the reaction temperature in said catalyst bed and impairing the reaction efficiency as said reactants pass through said catalyst bed, the step which comprises intimately contacting said heated reactant stream comprising propene and water until said propene has been saturated with about 0.3 to 1.4 weight percent of water prior to introducing said reactant stream into said reactor in order to maintain a relatively steady reaction temperature and efficient conversion of said propene to said isopropyl alcohol in said reactor.

* * * * *